(12) United States Patent
Ray, II et al.

(10) Patent No.: US 9,724,315 B2
(45) Date of Patent: Aug. 8, 2017

(54) COMPOUNDED TRANSDERMAL PAIN MANAGEMENT

(75) Inventors: Jay Richard Ray, II, Conroe, TX (US); Charles D. Hodge, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 635 days.

(21) Appl. No.: 13/328,369

(22) Filed: Dec. 16, 2011

(65) Prior Publication Data

US 2013/0085171 A1 Apr. 4, 2013

Related U.S. Application Data

(63) Continuation of application No. PCT/US2011/054324, filed on Sep. 30, 2011.

(60) Provisional application No. 61/541,716, filed on Sep. 30, 2011.

(51) Int. Cl.
| | |
|---|---|
| *A61K 31/135* | (2006.01) |
| *A61K 31/192* | (2006.01) |
| *A61K 31/195* | (2006.01) |
| *A61K 31/4168* | (2006.01) |
| *A61K 31/167* | (2006.01) |
| *A61K 31/197* | (2006.01) |
| *A61K 9/00* | (2006.01) |
| *A61K 47/02* | (2006.01) |
| *A61K 9/06* | (2006.01) |

(52) U.S. Cl.
CPC .......... *A61K 31/135* (2013.01); *A61K 9/0014* (2013.01); *A61K 9/06* (2013.01); *A61K 31/167* (2013.01); *A61K 31/192* (2013.01); *A61K 31/195* (2013.01); *A61K 31/197* (2013.01); *A61K 31/4168* (2013.01); *A61K 47/02* (2013.01)

(58) Field of Classification Search
CPC .. A61K 31/135; A61K 31/192; A61K 31/195; A61K 31/4168
USPC .............. 514/561, 401, 570, 646, 647, 656; 424/449
See application file for complete search history.

(56) References Cited

U.S. PATENT DOCUMENTS

| | | | |
|---|---|---|---|
| 6,248,789 B1 * | 6/2001 | Weg .............................. 514/647 |
| 6,410,062 B1 * | 6/2002 | Callaghan et al. ........... 424/764 |
| 8,535,738 B2 * | 9/2013 | Collins et al. ................ 424/750 |
| 2004/0265364 A1 * | 12/2004 | Ozturk et al. ................ 424/449 |
| 2009/0162421 A1 | 6/2009 | Geisslinger et al. |
| 2010/0184817 A1 | 7/2010 | Wolicki |

FOREIGN PATENT DOCUMENTS

| | | |
|---|---|---|
| EP | 0964552 A1 * | 3/2008 |
| JP | 7309749 * | 11/1995 |

OTHER PUBLICATIONS

JP7309749, Itaru Nov. 1995, English machine translation pp. 1-7.*
Abstract Only: Merskey H., Pharmacological approaches other than opioids in chronic non-cancer pain management, Acta Anaethesiol Scand, Jan. 1997, 41 (1 Pt 2), 187-190.
Abstract Only: Dissanayake et al., Spermine modulation of specific [3H]-gabapentin binding to the detergent-solubilized porcine cerebral cortex alpha 2 delta calcium channel subunit, Br J Pharmacol, Mar. 1997, 120(5), 833-840.
Abstract Only: Boardman et al., Topical gabapentin in the treatment of localized and generalized vulvodynia, Sep. 2008, 112(3): 579-585.
Prommer, Eric E., Topical analgesic combinations for bortezomib neuropathy, Journal of Pain and Symptom Management, Mar. 2009, 37(3), pp. e3-e5.
Abstract Only: Guindon et al., Recent advances in the pharmacological management of pain, Drugs, 2007, 67(15), 2121-2133.
Alsarra, Ibrahim A., Evaluation of proniosomes as an alternative strategy to optimize piroxicam transdermal delivery, Journal of Microencapsulation, 2008, 1-7, iFirst.
Penzes et al., Topical absorption of piroxicam from organogels—in vitro and in vivo correlations, International Journal of Pharmaceutics, 2005, 298, 47-54.
Abstract Only: Park et al., Transdermal delivery of piroxicam using microemulsions, Arch Pharm Res., Feb. 2005, 28(2), 243-248.
Abstract Only: Hong et al., Suprascapular nerve block or a piroxicam patch for shoulder tip pain after day case laparoscopic surgery, Eur J Anaesthesiol, Mar. 2003, 20(3), 234-238.
Doliwa et al., Transdermal Iontophoresis and skin retention of piroxicam from gels containing piroxicam: hydroxypropyl-beta-cyclodextrin complexes, Drug Development and Industrial Pharmacy, 2001, 27(8), 751-758, Marcel Dekker, Inc.
Abstract Only: Cordero et al., In vitro based index of topical anti-inflammatory activity to compare a series of NSAIDs, Eur J Pharm Biopharm, Mar. 2001, 51(2), 132-142.
Abstract Only: Ritchie LD, A clinical evaluation of flurbiprofen LAT and piroxicam gel: a multicentre study in general practice, Clin Rheumatol, May 1996, 15(3), 243-247.

(Continued)

*Primary Examiner* — Jennifer M Kim
(74) *Attorney, Agent, or Firm* — Akerman LLP

(57) ABSTRACT

The present embodiments relate to topically delivered medication (compounded) for treatment of pain, inflammation, muscle fatigue, spasms, and/or other ailments. A transdermal cream may provide the effective topical administration of multiple medications simultaneously. The transdermal cream may include a salt load of approximately 30% or greater. The transdermal cream may include a unique base composition such that the transdermal cream may be able to remain stable and avoid degradation for six months or more and capable of effective delivery of active ingredient concentrations exceeding approximately 40% or more of the total formulation weight. The active ingredients may include a nerve depressant, NSAID, muscle relaxant, opiate agonist, local anesthetic, NMDA receptor antagonist, and a tricyclic antidepressant. In one embodiment, the transdermal cream may comprise ketamine HCL, gabapentin, clonidine HCL and baclofen. The transdermal cream may deliver an enhanced topical delivery flux of ketamine via a single transdermal application.

1 Claim, 6 Drawing Sheets

(56) References Cited

OTHER PUBLICATIONS

Abstract Only: Marks et al., Plasma and cutaneous drug levels after topical application of piroxicam gel: a study in healthy volunteers, 1994, 7(6), 340-344.
Abstract Only: Russell AL., Piroxicam 0.5% topical gel compared to placebo in the treatment of acute soft tissue injuries: a double-blind study comparing efficacy and safety, Clin Invest Med, Feb. 1991, 14(1), 35-43.
Abstract Only: Akinturk et al., Effect of piroxicam gel for pain control and inflammation in Nd:YAG 1064-nm laser hair removal, J Eur Acad Dermatol Veneraol, Mar. 2007, 21(3), 380-383.
Abstract Only: Attia et al., Transbuccal permeation, anti-inflammatory activity and clinical efficacy of piroxicam formulated in different gels, Int J Pharm, May 19, 2004, 276(1-2), 11-28.
Abstract Only: Dutta et al., Piroxicam gel, compared to EMLA cream is associated with less pain after venous cannulation in volunteers, Can J Anaesth, Oct. 2003, 50(8), 775-778.
Abstract Only: Ambade KW, Formulation and evaluation of flurbiprofen microemulsion, Curr Drug Deliv., Jan. 2008, 5(1), 32-41.
Bhaskar et al., Lipid nanoparticles for transdermal delivery of flurbiprofen: formulation, in vitro, ex vivo and in vivo studies, Lipids in Health and Disease, Feb. 26, 2009, 8(6), 1476-1511.
Abstract Only: Pelfini et al., Flurbiprofen in gel: study of acceptability, tolerability and evaluation of its allergenic potential, G Ital Dermatol Venereol, Sep. 1989, 124(9), XLIII-XLVI.
Abstract Only: Suresh et al., Intracrevicular application of 0.3% Flurbiprofen gel and 0.3% Triclosan gel as anti-inflammatory agent. A comparative clinical study, Indian J Dent Res., Apr.-Jun. 2001, 12(2), 105-112.
Abstract Only: El Gendy et al., In vitro release studies of flurbiprofen from different topical formulations, Drug Dev Ind Pharm, Aug. 2002, 28(7), 823-31.
Esparza et al., Topical ketoprofen TDS patch versus diclofenac gel: efficacy and tolerability in benign sport related soft-tissue injuries, Br J Sports Med, 2007, 41, 134-139.
Abstract Only: Mazia Res B., Topical ketoprofen patch, Drugs R D, 2005, 6(6), 337-344.
Abstract Only: Audeval-Gerard et al., Pharmacokinetics of ketoprofen in rabbit after a single topical application, Eur J Drug Metab Pharmacokinet, Jul.-Dec. 2000, 25(3-4), 227-230.
Abstract Only: Moretti et al. In vitro release and antiinflammatory activity of topical formulations of ketoprofen, Boll Chim Farm, Mar.-Apr. 2000, 139(2), 67-72.
Abstract Only: Airaksinen et al., Ketoprofen 2.5% gel versus placebo gel in the treatment of acute soft tissue injuries, Int J Clin Pharmacol Ther Toxicol, Nov. 1993, 31(11) 561-563.
Abstract Only: Baixauli et al., Percutaneous treatment of acute soft tissue lesions with naproxen gel and ketoprofen gel, J Int Med Res, Sep.-Oct. 1990, 18(5), 372-378.
Abstract Only: Matucci-Cerinic et al., Ketoprofen vs etofenamate in a controlled double-blind study: evidence of topical effectiveness in soft tissue rheumatic pain, Int J Clin Pharmacol Res., 1988, 8(3), 157-160.
Abstract Only: Moghadamnia et al., Evaluation of the effect of locally administered amitriptyline gel as adjunct to local anesthetics in irreversible pulpitis pain, Jan.-Mar. 2009, 20(1), 3-6.
Sandroni et al., Combination gel of 1% amitriptyline and 0.5% ketamine to treat refractory erythromelalgia pain: a new treatment option?, Arch Dermatol, Mar. 2006, 142, 283-286.
Abstract Only: Sawynok et al., Peripheral antinociceptive actions of desipramine and fluoxetine in an inflammatory and neuropathic pain test in the rat, Pain, Aug. 1999, 82(2), 149-158.
Abstract Only: Scott et al., Use of transdermal amitriptyline gel in a patient with chronic pain and depression, Pharmacotherapy, Feb. 1999, 19(2) 236-239.
Abstract Only: Sakai et al., Quantitative and selective evaluation of differential sensory nerve block after transdermal lidocaine, Anesth Anaig., Jan. 2004, 98(1), 248-251.
Abstract Only: Taddio et al., Lidocaine-prilocaine cream versus tetracaine gel for procedural pain in children, Ann Pharmacother, Apr. 2002, 36(4), 687-692.
Abstract Only: Rowbotham et al., Topical lidocaine gel relieves postherpetic neuralgia, Ann Neurol, Feb. 1995, 37(2), 246-253.
Abstract Only: Shimoda et al., Transdermal application of 10% lidocaine-gel for management of pain associated with herpes zoster, Masui, Aug. 1993, 42(8), 1171-1176.
Abstract Only: Vadivelu et al., Recent advances in postoperative pain management, Yale J Biol Med, Mar. 2010, 83(1), 11-25.
Okon, Tomasz MD, Ketamine: An introduction for the pain and palliative medicine physician, Pain Physician, May 2007, 10, 493-500.
Abstract Only: Kronenberg RH., Ketamine as an analgesic: parenteral, oral, rectal, subcutaneous, transdermal and intranasal administration, J Pain Palliat Care Pharmacother, 2002, 16(3), 27-35.
Azevedo et al., Transdermal ketamine as an adjuvant for postoperative analgesia after abdominal gynecological surgery using lidocaine epidural blockade, Anesth Analg, 2000, 91, 1479-1482, International Anesthesia Research Society.
Vranken, Jan H., Mechanisms and treatment of neuropathic pain, Central Nervous System Agents in Medicinal Chemistry, 2009, 9, 71-78, Bentham Science Publishers Ltd.
Abstract Only: Canbay et al., Topical ketamine and morphine for post-tonsillectomy pain, Eur J Anaesthesiol, Apr. 2008, 25(4), 287-292.
Lynch et al., Topical amitriptyline and ketamine in neuropathic pain syndromes: An open-label study, The Journal of Pain, Oct. 2005, 6(10), 644-649, The American Pain Society.
Abstract Only: Gammaitoni et al., Topical ketamine gel: possible role in treating neuropathic pain, Pain Med, Mar. 2000, 1(1), 97-100.
Abstract Only: Slatkin et al., Topical ketamine in the treatment of mucositis pain, Pain Med, Sep. 2003, 4(3), 298-303.
Abstract Only: Altman et al., Topical therapy for osteoarthritis: Clinical and pharmacologic perspectives, Postgrad Med, Mar. 2009, 121(2), 139-147.
Roth et al., Efficacy and safety of a topical diclofenac solution in the treatment of primary osteoarthritis of the knee: a randomized, double-blind, vehicle controlled clinical trial, Arch Intern Med, Oct. 11, 2004, 164, 2017-2023, American Medical Association.
Kneer et al., A multiple-dose, open-label, safety, compliance, and usage evaluation study of epicutaneously applied Diractin (ketoprofen in Transfersome) in joint/musculoskeletal pain or soft tissue inflammation, Current Drug Safety2009, 4, 5-10, Bentham Science Publishers, Ltd.
Abstract Only: Boardman et al., Topical gabapentin in the treatment of localized and generalized vulvodynia, Obstet Gynecol, Sep. 2008, 112(3), 579-585.
Abstract Only: Akinturk et al., A clinical comparison of topical piroxicam and EMLA cream in pain relief and inflammation in laser hair removal, Lasers Med Sci, Jul. 2009, 24(4), 535-538.
Underwood et al., Topical or oral ibuprofen for chronic knee pain in older people. The TOIB study, Health Technology Assessment, 2008, 12(22), iii-iv, ix-155, Gray Publishing.
Abstract Only: Heir et al., Use of topical medication in orofacial neuropathic pain: a retrospective study, Oral Surg Oral Med Oral Pathol Oral Radiol Endod, Apr. 2008, 105(4) 466-469.
Lehman et al., Effective use of topical amitriptyline hydrochloride 2.5% and ketamine hydrochloride 0.5% for analgesia in refractory proctodynia, J Drugs Dermatol, Sep. 2008, 7(9), 887-889, Journal of Drugs in Dermatology, Inc.
Abstract Only: Kolesnikov et al., Analgesic synergy between topical opioids and topical non-steroidal anti-inflammatory drugs in the mouse model of thermal pain, Jan. 2008, 579(1-3), 126-133.
Abstract Only: Zacher et al., Topical diclofenac and its role in pain and inflammation: an evidence-based review, Curr Med Res Opin, Apr. 2008, 24(4), 925-950.
Abstract Only: Argoff CE., Topical treatments for pain, Curr Pain Headache Rep., Aug. 2004, 8(4), 261-167.
Abstract Only: Ashfield T., The use of topical opioids to relieve pressure ulcer pain, Nurs Stand, Jul. 2005, 19(45), 90-92.

(56) References Cited

OTHER PUBLICATIONS

PCCA, T3 Sodium Dilution (1:1000), Fall 2011 Issue, Sep. 1, 2011, PCCA Webpage, http://ww.rxinsider.com/20ways/articles/pcca_article.pdf].

* cited by examiner

COMPOUNDED TRANSDERMAL PAIN MANAGEMENT

CROSS-REFERENCE TO RELATED APPLICATION

This patent application claims priority U.S. Provisional Patent Application No. 61/541,716, filed Sep. 30, 2011, the entirety of which is incorporated herein by reference.

FIELD OF THE INVENTION

The present application relates to pain management. In particular, the present application relates to compounded transdermal pain management.

BACKGROUND

Transdermal creams are employed to deliver medication to the skin of a patient. However, conventional transdermal creams may include various drawbacks. For instance, conventional transdermal creams may not support and/or include high concentrations of an active ingredient. Conventional transdermal creams may also exhibit low rates and/or total amounts of absorption for certain active ingredients into the skin, and/or separation of an active ingredient from a base when exposed to environmental extremes.

SUMMARY

The present embodiments may relate to topically delivered compounded medications for treatment of pain, inflammation, muscle fatigue, spasms, and/or other ailments. In one aspect, a transdermal cream or gel for the effective administration of multiple medications simultaneously for one or more ailments may be provided. The transdermal cream may include a high concentration of one or more active ingredients. The transdermal cream may include a unique base composition and satisfactorily carry a salt load of approximately 30% or greater. The transdermal cream may be able to remain stable and/or avoid degradation for six months or longer, and be capable of effective delivery of active ingredient concentrations exceeding approximately 30%, or preferably 40% or more, of the total formulation weight of the transdermal cream. The transdermal cream may be able to withstand extreme temperatures and avoid separation of the active ingredients from the base during storage. In one embodiment, the transdermal cream may comprise a base composition and multiple active ingredients, such as ketamine HCL, gabapentin, clonidine HCL, and/or baclofen.

In one aspect, a pharmaceutical composition for a transdermal cream may be provided. The pharmaceutical composition may permit the topical administration of multiple medications simultaneously to address one or more ailments. The pharmaceutical composition may (1) exhibit resiliency in the presence of at least a 30% salt load, and (2) be able to remain stable and/or avoid degradation for six months or more. The pharmaceutical composition may be capable of effective delivery of active ingredient concentrations exceeding approximately 40% of the total formulation weight.

In another aspect, a transdermal cream may be provided. The transdermal cream may provide for the topical administration of multiple medications simultaneously. The transdermal cream may comprise a salt load of approximately 30% or greater. The transdermal cream may be able to remain stable and/or avoid degradation for six months or more. The transdermal cream may be capable of effective delivery of active ingredient concentrations exceeding approximately 20%, approximately 30%, or preferably exceeding approximately 40% or more, of the total formulation weight of the transdermal cream.

In another aspect, a transdermal cream may be provided. The transdermal cream may provide for the topical administration of multiple medications simultaneously, including ketamine, via a base composition to address various ailments. The transdermal cream may provide for greater than approximately 50% permeation of ketamine beyond the stratum corneum after a single dose is administered topically via the base composition. The transdermal cream may facilitate a maximum mean flux of greater than approximately 3.5 µg/cm$^2$/hr of percutaneous absorption of ketamine through the human skin within approximately 4 to approximately 10 hours after commencing a single dose via a topical administration using the transdermal cream. The transdermal cream may comprise the base composition and multiple active ingredients, such as ketamine HCL, gabapentin, clonidine HCL, and/or baclofen.

In another aspect, a compounded transdermal pain management program may be provided. The compounded transdermal pain management program may include providing a base composition, such as the unique base composition disclosed herein. The compounded transdermal pain management program may include providing, within the base composition, several medications that address different ailments. The medications may be mixed with the base composition for topical administration to a patient. The medications may include one or more NSAIDs (Non-Steroidal Anti-Inflammatory Drugs), such as propionic or acetic acids; one or more muscle relaxants, such as baclofen or cyclobenzaprine; one or more opioid or opiate agonists, such as C2 or C3 opiate agonists, or tramadol; one or more local anesthetics, such as lidocaine, prilocalne, or benzocaine; one or more NMDA (N-Methyl-D-aspartate) receptor antagonists, such as ketamine; one or more tricyclic antidepressants, such as amitriptyline; and/or one or more nerve depressants, such as gabapentin, topiramate, or lamotrigine. The medications may comprise approximately 20%, approximately 30%, or approximately 40% or more of a transdermal cream by weight.

In another aspect, a compounded transdermal pain management program for the topical administration of multiple medications simultaneously may comprise providing a transdermal cream; and providing several medications within the transdermal cream for topical administration to a patient. The several medications may include: (1) at least one local anesthetic, such as lidocaine and/or prilocalne, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID (Non-Steroidal Anti-Inflammatory Drug), such as flurbiprofen or nabumetone, in an amount between approximately 5.0% and approximately 25.0% of the transdermal cream by weight; and (4) at least one muscle relaxant, such cyclobenzaprine, in an amount between approximately 0.5% and approximately 4.0% of the transdermal cream by weight such that multiple ailments may be addressed simultaneously. In one embodiment, the transdermal cream may comprise, by weight of the transdermal cream, approximately 2.0% lidocaine, approximately 2.0% prilocalne, approximately 6.0% gabapentin, approximately 1.0% cyclobenzaprine, and approximately 10.0% flurbiprofen or approximately 20% nabumetone. The several medications may also include an opioid or opiate agonist, a tricyclic antidepressant, and/or a NMDA receptor antagonist.

In another aspect, a compounded transdermal pain management program for the topical administration of multiple medications simultaneously may comprise providing a transdermal cream; and providing several medications within the transdermal cream for topical administration to a patient. The several medications may include: (1) at least one local anesthetic, such as lidocaine and/or prilocalne, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID (Non-Steroidal Anti-Inflammatory Drug), such as flurbiprofen or nabumetone, in an amount between approximately 5.0% and approximately 25.0% of the transdermal cream by weight; and (4) at least one tricyclic antidepressant, such as amitriptyline, in an amount between approximately 0.5% and approximately 4.0% of the transdermal cream by weight. In one embodiment, the transdermal cream may comprise, by weight of the transdermal cream, approximately 2.0% lidocaine, approximately 2.0% prilocalne, approximately 6.0% gabapentin, approximately 1.0% amitriptyline, and approximately 10.0% flurbiprofen or approximately 20.0% nabumetone. The several medications may also include an opioid or opiate agonist, a muscle relaxant, and/or a NMDA receptor antagonist.

The above-described and other features and advantages of the present disclosure will be appreciated and understood by those skilled in the art from the following detailed description, drawings, and appended claims.

BRIEF DESCRIPTION OF THE DRAWINGS

There is shown in the drawings embodiments which are presently preferred, it being understood, however, that the invention can be embodied in other forms without departing from the spirit or essential attributes thereof.

DETAILED DESCRIPTION OF THE INVENTION

Figure 1:
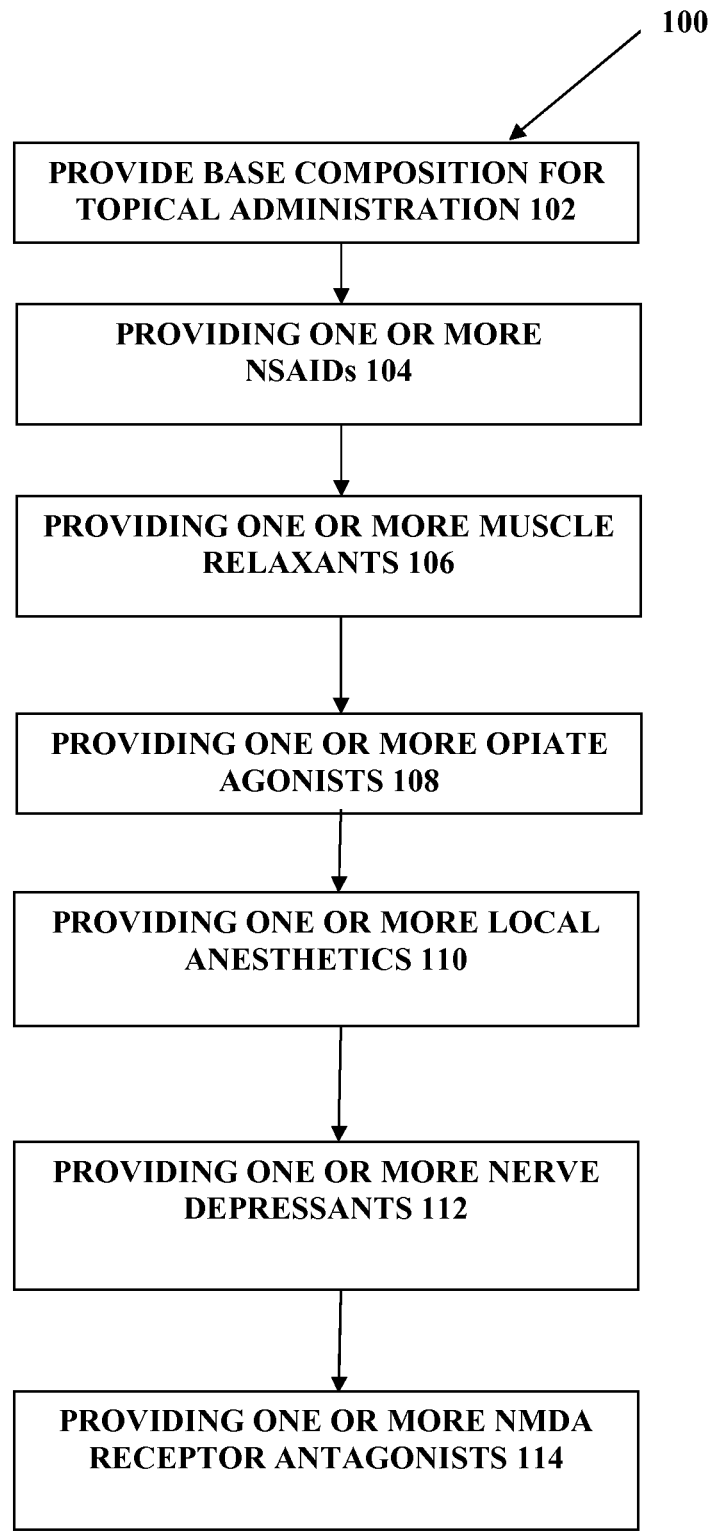
FIG. 1 depicts an exemplary method of employing a compounded transdermal pain management program.

The present embodiments may relate to topically delivered compounded medications, such as for the treatment of pain, inflammation, muscle fatigue, spasms, and/or other ailments. In one aspect, the present embodiments relate to a transdermal cream or gel for the topical administration of multiple medications for different ailments simultaneously. The transdermal cream may include a salt load of approximately 30% of the transdermal cream or greater. The transdermal cream may include a unique base composition that allows the transdermal cream to remain stable and avoid degradation for six months or longer.

The transdermal cream may be capable of providing enhanced effective delivery of active ingredient concentrations exceeding approximately 20%, approximately 30%, or preferably approximately 40% or more, of the total formulation weight of the transdermal cream and/or base composition. The transdermal cream may be able to withstand extreme temperatures and avoid separation of the active ingredients from the base composition. For instance, the transdermal cream may be able to withstand extreme temperatures exceeding room temperature, such as approximately 72° F. or greater, and still remain stable and avoid substantial or all separation of a base and the active ingredients. In one embodiment, the transdermal cream may comprise ketamine HCL, gabapentin, clonidine HCL, baclofen, and/or other active ingredients.

In one aspect, a pharmaceutical composition for a transdermal cream may be provided. The pharmaceutical composition may permit the topical administration of multiple medications simultaneously to address one or more ailments. The pharmaceutical composition may (1) exhibit resiliency in the presence of a salt load of approximately 30% of the pharmaceutical composition or greater, and (2) be able to remain stable and/or avoid degradation for six months or more. The salt load may be in the form of ketamine HCL. The pharmaceutical composition may be capable of effective delivery of active ingredient concentrations exceeding approximately 30%, and preferably approximately 40% or more, of the total formulation weight. The pharmaceutical composition may provide for approximately 50% or greater permeation of an active ingredient, such as ketamine, beyond the stratum corneum.

In another aspect, a transdermal cream may be provided. The transdermal cream may provide for the topical administration of multiple medications simultaneously, including ketamine, to address one or more ailments. The transdermal cream may provide for greater than approximately 50% permeation of ketamine beyond the stratum corneum after a single dose is administered topically via a base composition. The transdermal cream may facilitate a maximum mean flux of greater than approximately 3.5 $\mu g/cm^2/hr$ of percutaneous absorption of ketamine through the human skin within approximately 4 to approximately 10 hours after commencing a single dose via a topical administration using the transdermal cream. The transdermal cream may comprise ketamine HCL, gabapentin, clonidine HCL, baclofen, and/or other active ingredients.

A compounded transdermal pain management program may be provided. The compounded transdermal pain management program may include providing a base composition, such as the unique base composition disclosed herein. The compounded transdermal pain management program may include providing, within the base composition, several medications that address different ailments. The medications may be mixed with the base composition for topical administration to a patient. The medications may include one or more NSAIDs, such as propionic or acetic acids; one or more muscle relaxants, such as baclofen or cyclobenzaprine; one or more opioid or opiate agonists, such as C2 or C3 opiate agonists, or tramadol; one or more local anesthetics, such as lidocaine, prilocalne, or benzocaine; one or more nerve depressants, such as gabapentin, topiramate, or lamotrigine; and/or one or more NMDA (N-Methyl-D-aspartate) receptor antagonists, such as ketamine. The medications may comprise approximately 20%, approximately 30%, or approximately 40% or more of a transdermal cream or gel by weight.

I. Compounded Transdermal Pain Management

The present embodiments may relate to a compounded transdermal pain management program. A compounded transdermal pain management program may address a several ailments simultaneously. The program may provide pain treatments that (1) may not include oral therapies; (2) may have minimal side effects; and (3) may avoid drug-drug interactions from concomitant therapies. The latter may become a greater concern with an aging population that may have poorer blood circulation and be using an increased number of oral therapies resulting in ever increasing drug-drug interactions—both of which may cause pain management therapies to be difficult to be prescribed. The program may provide patients with the highest quality-of-life possible with the lowest side-effect profile possible.

FIG. 1 depicts an exemplary method of employing a compounded transdermal pain management program 100. The compounded transdermal pain management program 100 may include providing a base composition 102; and within the base composition, providing: one or more NSAIDs 104; one or more muscle relaxants 106; one or more opioid or opiate agonists 108; one or more local anesthetics 110; one or more nerve depressants 112; and/or one or more NMDA receptor antagonists 114. The compounded transdermal pain management program may include additional, fewer, or alternate steps and/or ingredients.

The compounded transdermal pain management program 100 may include providing a base composition 102. The base composition may include the base ingredients discussed herein below, including the base ingredients identified in Table I below. The base composition may include additional, fewer, or alternate ingredients.

The compounded transdermal pain management program 100 may provide, such as within the base composition, one or more NSAIDs (Non-Steroidal Anti-Inflammatory Drugs/medications) 104. NSAIDs may block the synthesis of prostaglandins by inhibiting cyclooxygenase-2 (COX-2) and/or cyclooxygenase-1 (COX-1). All classes of NSAIDs may block both COX-1 and COX-2 except for the last class which is specifically delineated out as COX-2 inhibitors Inhibition of COX-2 may produce the positive effects of NSAIDs, while blocking COX-1 may cause the side effects of stomach upset, increased stomach acid, and the like. The compounded transdermal pain management program may include COX-1 and/or COX-2 inhibitors.

Blocking the synthesis of prostaglandins (COX-2 specifically) may decrease inflammation, swelling, and pain associated with the production of the same. When one class of NSAIDs fails to produce the desired response, it may be appropriate to shift a patient to a different class of non-steroidal anti-inflammatory medications. A patient who is prescribed a medication in one particular class that fails to achieve the desired response may also fail therapy on a medication that is in that same class. Switching classes of NSAIDs may be appropriate when a failure in one subset is seen.

NSAIDs that may be used with the compounded transdermal pain management program, as well as the transdermal creams and/or base composition disclosed herein, may include: (1) salicylic acid derivatives—aspirin, diflunisal, salsalate, and trilisate; (2) propionic acids—flurbiprofen, ibuprofen, ketoprofen, naproxen, and oxaprozin; (3) acetic acids—diclofenac, etodolac, indomethacin, ketorolac, nabumetone, sulindac, and tolmetin; (4) fenamates—meclofenamate; (5) oxicams—meloxicam and piroxicam; and (6) COX-2 inhibitors—celecoxib, rofecoxib, and valdecoxib. The transdermal cream may include an amount of NSAIDs ranging from approximately 0.01% to approximately 20% by weight.

The compounded transdermal pain management program 100 may provide, such as within the base composition, one or more muscle relaxants 106. Muscle relaxant medications may produce muscle relaxation by blocking interneuronal activity in the descending reticular formation and/or spinal cord. Each different medication may have it's own set of nuances with the most dominant ones (at least in reference to oral therapies) being carisoprodol and cyclobenzaprine. Available muscle relaxants that the compounded transdermal pain management program, as well as the transdermal creams and base composition disclosed herein, may employ include, but are not necessarily limited to, baclofen, carisoprodol, chlorzoxazone, cyclobenzaprine, dantrolene, diazepam, metaxalone, methocarbamol, orphenadrine, quinine sulfate, and/or tizanidine. The transdermal cream may include an amount of muscle relaxants ranging from approximately 0.01% to approximately 20% by weight.

The compounded transdermal pain management program 100 may provide, such as within the base composition, one or more opioid or opiate agonists 108. Opiate agonists include medications that may directly bind to opiate receptors in the body whose principal therapeutic action is analgesia. Pharmacological effects of opioid agonists may include anxiolysis, euphoria, feelings of relaxation, respiratory depression, constipation, miosis, and cough suppression, as well as analgesia. C2 opiate agonists may include oxycodone, morphine, methadone, hydromorphone, and fentanyl. C3 opiate agonists may include hydrocodone, codeine, propoxyphene, butalbital, and pentazocine. Tramadol, although not a narcotic medication, may act on the opiate receptor site to cause pain relief with the same identified mechanism of action of C2 and C3 opiate agonists. However, the levels of effectiveness, as well as physical dependency, may be more depressed with tramadol than with the others. The compounded transdermal pain management program, as well as the transdermal creams and base composition disclosed herein, may employ C2 and C3 opiate agonists, such as the ones named above, and/or tramadol. The transdermal cream may include an amount of opioid or opiate agonists ranging from approximately 0.01% to approximately 20% by weight.

The compounded transdermal pain management program 100 may provide, such as within the base composition, one or more local anesthetics 110. Local anesthetics may include medications that are applied to intact skin and provide dermal analgesia by the release of the medication(s) from the cream base (or from a patch) into the epidermal and dermal layers of the skin, and by the accumulation of the drug in the vicinity of the dermal pain receptors and nerve endings. Local anesthetics may stabilize neuronal membranes by inhibiting the ionic fluxes required for the initiation and conduction of impulses, thereby effecting local anesthetic action. Primary examples of local anesthetics that the compounded transdermal pain management program, as well as the transdermal creams and base composition disclosed herein, may employ include, but are not limited to, lidocaine, prilocalne, benzocaine, and/or tetracaine. The transdermal cream may include an amount of local anesthetics ranging from approximately 0.01% to approximately 20% by weight.

The compounded transdermal pain management program 100 may provide, such as within the base composition, one or more nerve depressants 112. Nerve depressants include medications that may have a mechanism of action largely unknown. In animal models of analgesia, nerve depressants may prevent allodynia (pain related behavior in response to a normally innocuous stimulus) and hyperalgesia (exaggerated response to painful stimuli). Nerve depressants may also decrease pain-related responses after peripheral inflammation.

The compounded transdermal pain management program may provide for therapy with regard to a host of different localized nerve problems. The mechanism by which gabapentin works orally may also work with some topical therapies, such as the base composition disclosed herein. Nerve depressants that the compounded transdermal pain management program, as well as the transdermal creams and base composition disclosed herein, may employ include gabapentin, topiramate, lamotrigine, and/or others. The transdermal cream may include an amount of nerve depressant ranging from approximately 0.01% to approximately 20% by weight, such as approximately 10% by weight.

The compounded transdermal pain management program 100 may provide, such as within the base composition, one or more NMDA receptor antagonist 114, such as ketamine. Ketamine is a drug used in human and veterinary medicine. Pharmacologically, ketamine is classified as a NMDA receptor antagonist. At high, fully anesthetic level doses, ketamine may bind to opioid μ receptors and sigma receptors. Like other drugs of this class, such as tiletamine and phencyclidine (PCP), ketamine may induce a state referred to as "dissociative anesthesia." Because ketamine is a phencyclidine analogue, it may have psychological adverse effects found with that hallucinogen. Although ketamine is frequently used as a veterinary anesthetic, it is used more frequently in children than in adults. The psychotomimetic effects have prompted the DEA to classify ketamine as a Schedule III Controlled Substance. However, it is believed that ketamine may demonstrate no or only mild psychotomimetic effects when dosed at sub-anesthetic doses. The transdermal cream may include an amount of a NMDA receptor antagonist ranging from approximately 0.01% to approximately 40% by weight, such as approximately 30% by weight.

Neuropathic pain may be resistant to opioids, so the compounded transdermal pain management program may also use other medication classes, such as tricyclic antidepressants, anticonvulsants, non-steroidal anti-inflammatories, and/or local anesthetics. Still, ketamine may be useful because of its NMDA receptor activity (antagonism). Activity on NMDA receptor may be the same as that produced by dextromethorphan. The current application of ketamine in the base composition/topical gel or cream disclosed herein stems from the theory that ketamine has peripheral action at both opioid and Na+ and K+ channels.

Generally, ketamine should only be recommended for refractory pain, i.e., pain that goes beyond the scope and bounds of traditional treatment therapies. FDA approved usages should also be kept in mind. The FDA approved adult usage is dissociative sedation with dosing of 1-2 mg/kg IV over 1-2 minutes or 4-5 mg/kg IM, and the FDA approved pediatric usage is dissociative sedation with dosing of 1-2 mg/kg IV over 1-2 minutes or 4-5 mg/kg IM. The standard dosing of ketamine may be around 400 mg, and not more often than 5 times daily, based upon a patient that weighs about 176 pounds.

II. Exemplary Base Composition

The present transdermal cream embodiments include a unique base composition that is an extension of the popular and trusted base Lipoderm®. The base composition may provide superior emulsion stability with high active ingredient concentrations. The base composition was engineered to improve and enhance the active ingredient carrying capacity of Lipoderm®. Enhanced active ingredient carrying capacity may be desirable when transdermally treating certain conditions, such as neuropathic pain, and/or multiple conditions via a single transdermal cream.

The base composition may allow physicians to prescribe increased amounts of multiple active ingredients to be administered topically. The base composition may allow for higher single active ingredient percentages to reduce the amount of applied cream needed by patients to reach a given amount of medication administered. The base composition may allow for higher permeation percentages for the active ingredients, which may also reduce the amount of applied cream needed to reach a desired dosage of medication.

With conventional base compositions, medicine providers who ship medications to patients, or serve patients who carry their creams with them all the time, may experience issues with the creams separating (base from active) when exposed to environmental extremes. The base composition of the present embodiments may address these types of challenges without sacrificing the cosmetically elegant feel of Lipoderm®. The unique base composition disclosed herein has the trade name Lipoderm® ActiveMax™.

The base composition of the present embodiments was developed in part to show resiliency in the presence of high salt loads, such as ketamine HCL or other salts. For example, approximately 30% Ketamine HCL in the base composition disclosed herein demonstrated superior physicochemical attributes, such as remaining stable and elegant for six (6) months. In one embodiment, the base composition may be used with a transdermal cream that may provide a formulation with active ingredient concentrations exceeding approximately 30%, or approximately 40% or more, of the total formulation weight of the transdermal cream, and/or alleviate separation issues. The base composition may provide for increased stability in the presence of high active ingredient percentages.

Table I below lists the base ingredients for the preferred embodiment of the base composition disclosed herein. Other ingredient lists with additional, fewer, or alternate ingredients may be used.

TABLE I

| Base Lipoderm ® ActiveMax ™ Ingredients |
| --- |
| Water |
| Cetearyl Alcohol |
| *Plukenetia Volubilis* Seed Oil |
| Isopropyl Myristate |
| Propylheptyl Caprylate |
| Sodium Stearoyl Glutamate |
| PEG-8/SMDI Copolymer |
| PEG-100 Stearate |
| Glyceryl Stearate |
| Glycerin |
| Tocopheryl Acetate |
| Lecithin |
| Hydrogenated Lecithin |
| *Populus Tremuloides* Bark Extract |
| *Lonicera Japonica* (Honeysuckle) Flower Extract |
| *Lonicera Caprifolium* (Honeysuckle) Flower Extract |
| Leuconostoc/Radish Root Ferment Filtrate |
| *Pentaclethra Macroloba* Seed Oil |

TABLE I-continued

Base Lipoderm ® ActiveMax ™ Ingredients

*Butyrospermum Parkii* (Shea) Butter
*Carthamus Tinctorius* (Safflower) Seed Oil
*Cocos Nucifera* (Coconut) Oil
Tocopherol
Ascorbyl Palmitate
Squalane
Ceramide 3
Alcohol
Caprylic/Capric Triglyceride
Xanthan Gum
Gluconolactone
Sodium Dehydroacetate
Disodium EDTA
BHT The most important ingredients of the base identified above are believed to include water, alcohol (preferably cetearyl alcohol), polyethylene glycol (PEG), glycerin, lecithin, shea butter, coconut oil, ascorbyl palmitate, xanthan gum, and disodium ethylenediaminetetraacetic acid (EDTA). In one aspect, a base may comprise or consist of water, cetearyl alcohol, PEG or various forms of PEG, glycerin, lecithin, shea butter, coconut oil, ascorbyl palmitate, xanthan gum, disodium EDTA, and/or other ingredients, including those listed above in Table I, to deliver several medications via a transdermal cream simultaneously. The several medications may comprise approximately 20%, approximately 30%, or approximately 40% or more of the transdermal cream by weight, with the remainder of the transdermal cream by weight being the base. Additional, fewer, or alternate ingredients may be used.

In another aspect, a transdermal cream comprising xanthan gum, PEG-8/SMDI copolymer, PEG-100 stearate, disodium EDTA, and/or other ingredients (including those listed in Table I above) may be used to topically deliver one or more NSAIDs, muscle relaxants, opiate agonists, local anesthetics, NMDA receptor antagonists, tricyclic antidepressants, and/or nerve depressants simultaneously. The transdermal cream may comprise from approximately 0.01% to approximately 40% by weight NMDA receptor antagonist, from approximately 0.01% to approximately 20% by weight nerve depressant, from approximately 0.01% to approximately 20% by weight of local anesthetic, from approximately 0.01% to approximately 20% by weight of muscle relaxant, from approximately 0.01% to approximately 20% by weight of opioid or opiate agonist, and/or from approximately 0.01% to approximately 20% by weight of NSAIDs.

For instance, the transdermal cream may comprise approximately 30% by weight of NMDA receptor antagonist (such as ketamine), approximately 10% by weight of nerve depressant (such as gabapentin), approximately 4% by weight of local anesthetics (such as lidocaine and/or prilocalne), between approximately 0.01% and approximately 5% of muscle relaxant (such as baclofen or cyclobenzaprine), between approximately 0.01% and approximately 5% of opioid agonist (such as tramadol), between approximately 0.01% and approximately 5% of a tricyclic antidepressant (such as amitriptyline), and/or approximately 10% of a NSAID (such as flurbiprofen). The total amount of the medications in the transdermal cream by weight may be greater than approximately 20%, approximately 30%, or approximately 40% or more, with the remainder of the transdermal cream being the base composition discussed herein.

In one embodiment, the transdermal cream comprising xanthan gum, PEG-8/SMDI copolymer, PEG-100 stearate, disodium EDTA, and/or other ingredients may include several medications, such as ketamine, gabapentin, topiramate, lamotrigine, clonidine, baclofen, lidocaine, prilocalne, tramadol, flurbiprofen, amitriptyline, cyclobenzaprine, ibuprofen, meloxicam, prioxicam, and/or other medications, including those mentioned herein. The medications, either individually or collectively, may comprise between approximately 0.01% and approximately 40% or more by weight of the transdermal cream.

III. Evaluation of Exemplary Transdermal Cream Compositions

The base composition disclosed herein, Lipoderm® ActiveMax™, has been proven to deliver four drugs, intact, simultaneously. An evaluation of the percutaneous absorption of ketamine HCL, gabapentin, clonidine HCL, and baclofen in both Lipoderm® and Lipoderm® ActiveMax™ into human trunk skin, in vitro, using the Franz skin finite dose model was performed. The study was designed to evaluate the percutaneous absorption harmacokinetics of ketamine HCL, gabapentin, clonidine HCL, and baclofen. Absorption was measured in human cadaver skin, in vitro, using the finite dose technique and Franz diffusion cells.

Ketamine HCL 5% w/w, gabapentin 10% w/w, clonidine HCL 0.2% w/w and baclofen 2% w/w, in Lipoderm® and Lipoderm® ActiveMax, were tested on triplicate sections from three different cadaver skin donors for the percutaneous absorption of ketamine HCL, gabapentin, clonidine HCL, and baclofen over a 48-hour dose period. At preselected times after dose application, the dermal receptor solution was removed in its entirety, replaced with fresh receptor solution, and an aliquot saved for subsequent analysis. In addition, the epidermis and dermis were recovered and evaluated for drug content. The samples were analyzed for ketamine HCL, gabapentin, clonidine HCL, and baclofen content by High Performance Liquid Chromatography (HPLC)/MS.

A. Methods and Procedures Utilized for Evaluation

The in vitro Franz skin finite dose model has proven to be a valuable tool for the study of percutaneous absorption and the determination of the pharmacokinetics of topically applied drugs. The model uses ex vivo animal, human cadaver, or surgical skin mounted in specially designed diffusion cells that allow the skin to be maintained at a temperature and humidity that match typical in vivo conditions. (See Franz, T. J., Percutaneous Absorption: On the Relevance of In Vitro Data. J. Invest. Dermatol, 1975, 64:190-195.)

A finite dose (e.g., 4-7 mg/cm$^2$) of formulation may be applied to the outer surface of the skin and drug absorption may be measured by monitoring its rate of appearance in the receptor solution bathing the inner surface of the skin. Data defining total absorption, rate of absorption, as well as skin content may be accurately determined in this model. The method has historic precedent for accurately predicting in vivo percutaneous absorption kinetics. (See Franz T. J., The Cadaver Skin Absorption Mode and the Drug Development Process. Pharmacopeial Forum 34(5): 1349-1356, 2008; see also Franz T. J., Lehman P. A., and Raney S., Use of Excised Human Skin to Assess the Bioequivalence of Topical Products. Skin Pharmacol Physiol 22:276-286, 2009.)

During the evaluation, percutaneous adsorption was measured using the in vitro cadaver skin finite dose technique. Human cadaver trunk skin without obvious signs of skin disease, obtained within approximately 24 to 48 hours of death, was used in this study. The skin was dermatomed, cryopreserved, sealed in a water-impermeable bag and stored at approximately −70° C. until the day of the experiment. Prior to use, the skin was thawed in approximately 37° C. water, then rinsed in water to remove any adherent blood or other material from the surface.

Skin from three donors was cut into multiple smaller sections large enough to fit on an approximately nominal 0.8 cm$^2$ Franz diffusion cells. The dermal chamber was filled to capacity with a reservoir solution of phosphate-buffered isotonic saline (PBS), pH 7.4±0.1, with 0.1% Oleth-20 and 0.008% Gentamicin, and the epidermal cell (chimney) left open to ambient laboratory conditions. All cells were mounted in a diffusion apparatus in which the dermal bathing solution was stirred magnetically at approximately 600 RPM and the skin surface temperature maintained at 32.0°±1.0° C.

To assure the integrity of each skin section, its permeability to tritiated water was determined before application of the test products. (See Franz T. J. and Lehman P. A., The Use of Water Permeability as a Means of Validation for Skin Integrity in In Vitro Percutaneous Absorption Studies. Abst. J. Invest. Dermatol 1990, 94:525.) Following a brief (0.5-1 hour) equilibrium period, $^3H_2O$ (NEN, Boston, Mass., sp. Act. ~0.5 µCi/mL) was layered across the top of the skin so that the entire exposed surface was covered (approximately 250 to 500 µL). After 5 minutes the $^3H_2O$ aqueous layer was removed. At 30 minutes, the receptor solution was collected and analyzed for radioactive content by liquid scintillation counting.

Just prior to dosing, a pre-dose sample was taken and the reservoir solution was replaced with a fresh solution of 1×PBS with 0.1% Oleth-20 and 0.008% Gentamicin. The chimney was removed from the Franz cell to allow full access to the epidermal surface of the skin. All formulations were then applied to the skin sections using a positive displacement pipette set to deliver 5 µL formulation/cm$^2$. The dose was spread across the surface with a glass rod. Five to ten minutes after application the chimney portion of the Franz cell was replaced. At pre-selected times after dosing (2, 4, 8, 12, 24, 32, and 48 hours), the reservoir solution was removed in its entirety, replaced with fresh reservoir solution, and a predetermined volume aliquot saved for subsequent analysis.

After the last sample was collected, the surfaces were washed twice (0.5 mL volume each) with 80:20 methanol: water to collect un-absorbed formulation from the surface of the skin. Following the surface cleanse, the skin was then removed from the diffusion cell, split into epidermis and dermis, and each skin sample extracted overnight using an appropriate extraction solvent, and analyzed for ketamine HCL, gabapentin, clonidine HCL, and baclofen content. Ketamine HCL, gabapentin, clonidine HCL, and baclofen concentrations were quantified in study samples using an HPLC/MS analytical method. Donor demographics are listed in Table II below.

TABLE II

Donor Demographics

| Donor ID | Age | Race | Sex |
|---|---|---|---|
| HR032809 | 72 | Black | Male |
| MC111306 | 58 | Caucasian | Male |
| MD110308 | 68 | Caucasian | Male |

The formulation used during the evaluation involved ketamine HCL, gabapentin, clonidine HCL, and baclofen, in an amount necessary to result in a concentration of 5% w/w, 10% w/w, 0.2% w/w and 2% w/w respectively, being added to the base compositions, along with 10% propylene glycol as a wetting agent, and mixed with the aid of an electronic mortar and pestle (EMP, 3 minutes at a setting of 7). The formulation was sheared twice using an ointment mill, at a setting of 2, and remixed with the EMP (1 minute at a setting of 5) to achieve accurate content uniformity. Potency was confirmed through the use of a High Performance Liquid Chromatograph (HPLC) with a photo diode array detector or Ultra High Performance Liquid Chromatograph (UHPLC) with a CAD detector.

B. Results

The data indicates that the base composition, Lipoderm® ActiveMax™, delivered ketamine HCL, gabapentin, clonidine HCL and baclofen, simultaneously (and intact), into and through human cadaver skin, in vitro. The data shows that ketamine HCL, gabapentin, clonidine HCL, and baclofen in the base composition may penetrate into and through ex vivo human trunk skin using the Franz finite dose model.

In particular, the absorption profiles indicate a rapid penetration to a peak flux for gabapentin and baclofen occurring approximately one hour after dose application, and between approximately four to approximately ten hours after dose application for ketamine Clonidine exhibited a rapid penetration to an initial peak flux occurring approximately one hour after dose application, but also a secondary peak at between approximately 28 and 40 hours, possibly due to a depot of some of the applied dose in the epidermis, followed by a slow decrease in flux afterward. (See FIGS. 2-6.) This one-of-a-kind study validates the ability of the base composition to deliver four drugs simultaneously through human skin and intact. This information is potentially of great value for pharmacists and physicians utilizing topical preparations for various pain syndromes.

Figure 2:
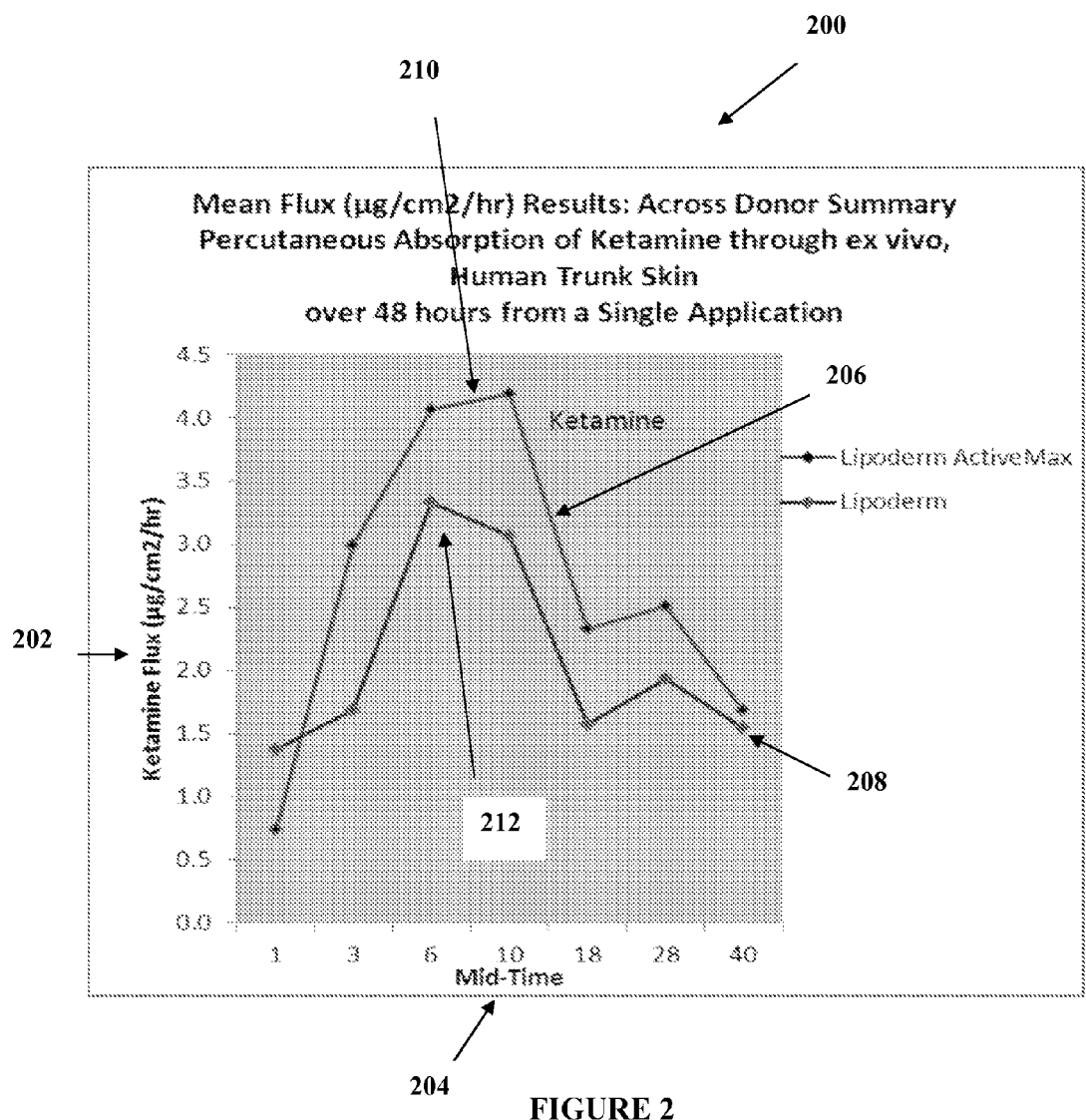
FIG. 2 depicts ketamine flux versus time exhibited during an exemplary evaluation of the exemplary transdermal cream embodiments discussed herein.

FIG. 2 depicts ketamine flux versus time exhibited during the exemplary evaluation of the exemplary transdermal cream embodiments discussed herein. In particular, FIG. 2 depicts a summary 200 of the mean flux (µg/cm$^2$/hr) results 202 of percutaneous absorption of ketamine through ex vivo, human trunk skin over 48 hours 204 from a single application. The ketamine mean flux graph using the base composition, Lipoderm® ActiveMax™ 206, yielded a ketamine flux of approximately 0.75 µg/cm$^2$/hr at about 1 hour after application, approximately 3.0 µg/cm$^2$/hr at about 3 hours after application, approximately 4.1 µg/cm$^2$/hr at about 6 hours after application, approximately 4.3 µg/cm$^2$/hr at about 10 hours after application, approximately 2.4 µg/cm$^2$/hr at about 18 hours after application, approximately 2.5 µg/cm$^2$/hr at about 28 hours after application, and approximately 1.9 µg/cm$^2$/hr at about 40 hours after application.

As shown in FIG. 2, the mean flux of ketamine through the skin using the base composition, Lipoderm® ActiveMax™ 206, was proven to exceed the mean flux of ketamine through the skin using Lipoderm® 208 for most of the 48 hours after a single application. As depicted, the mean flux of ketamine through the skin using the base composition, Lipoderm® ActiveMax™ 206, exceeded the mean flux of ketamine through the skin using Lipoderm® 208 within about 2 hours after a single application.

The maximum mean flux of ketamine 210 using the base composition 206 exceeded the maximum mean flux of ketamine 212 through the skin using Lipoderm® 208. The maximum mean flux of ketamine 210 using the base composition 206 was approximately 4.3 µg/cm$^2$/hr at about 10 hours after application, which occurred later after application than the maximum mean flux of ketamine 212 using Lipoderm® 208.

Figure 3:
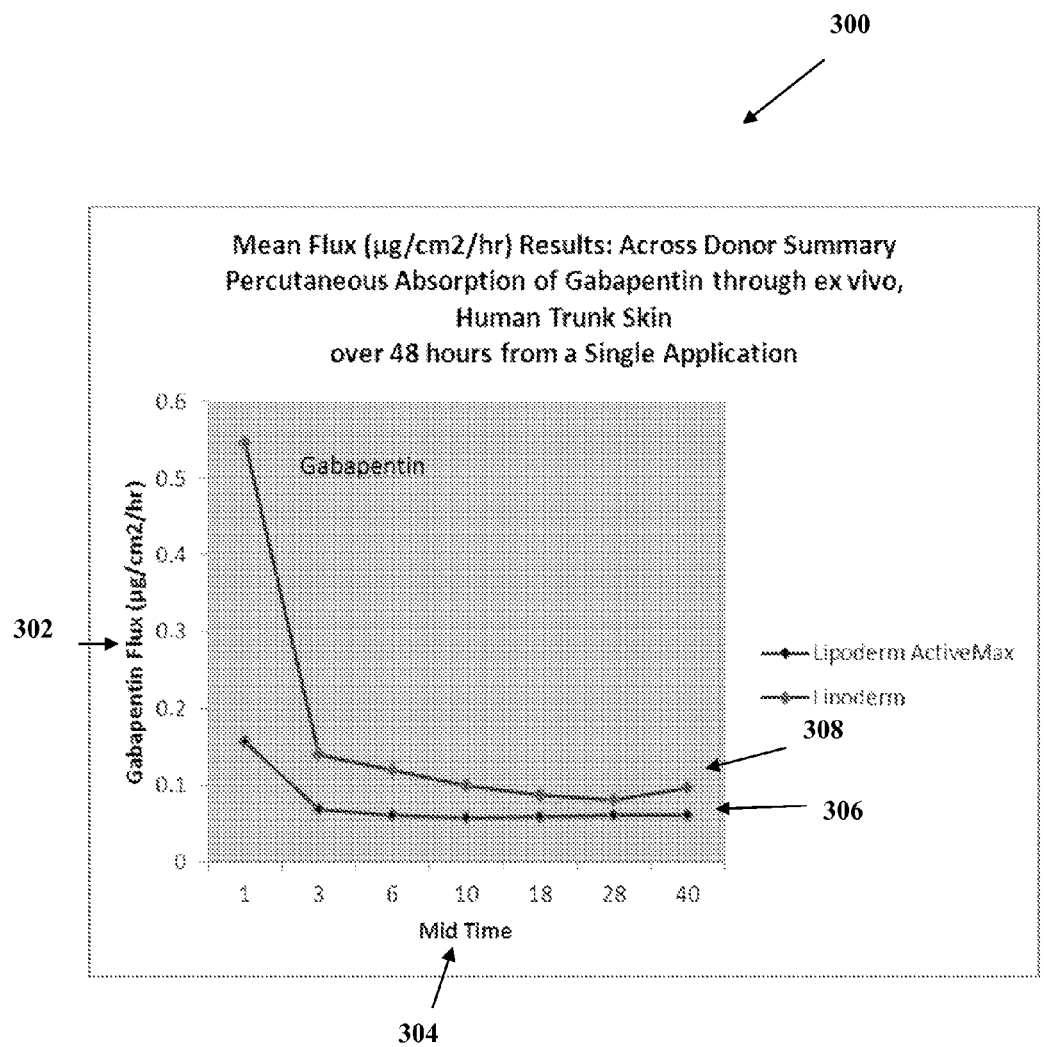
FIG. 3 depicts gabapentin flux versus time exhibited during the exemplary evaluation.

FIG. 3 depicts gabapentin flux versus time exhibited during the exemplary evaluation. In particular, FIG. 3 depicts a summary 300 of the mean flux ($\mu g/cm^2/hr$) 302 results of percutaneous absorption of gabapentin through ex vivo, human trunk skin over 48 hours 304 from a single application. Depicted are the mean flux of gabapentin through the skin using the base composition, Lipoderm® ActiveMax™ 306, and Lipoderm® 308.

Figure 4:
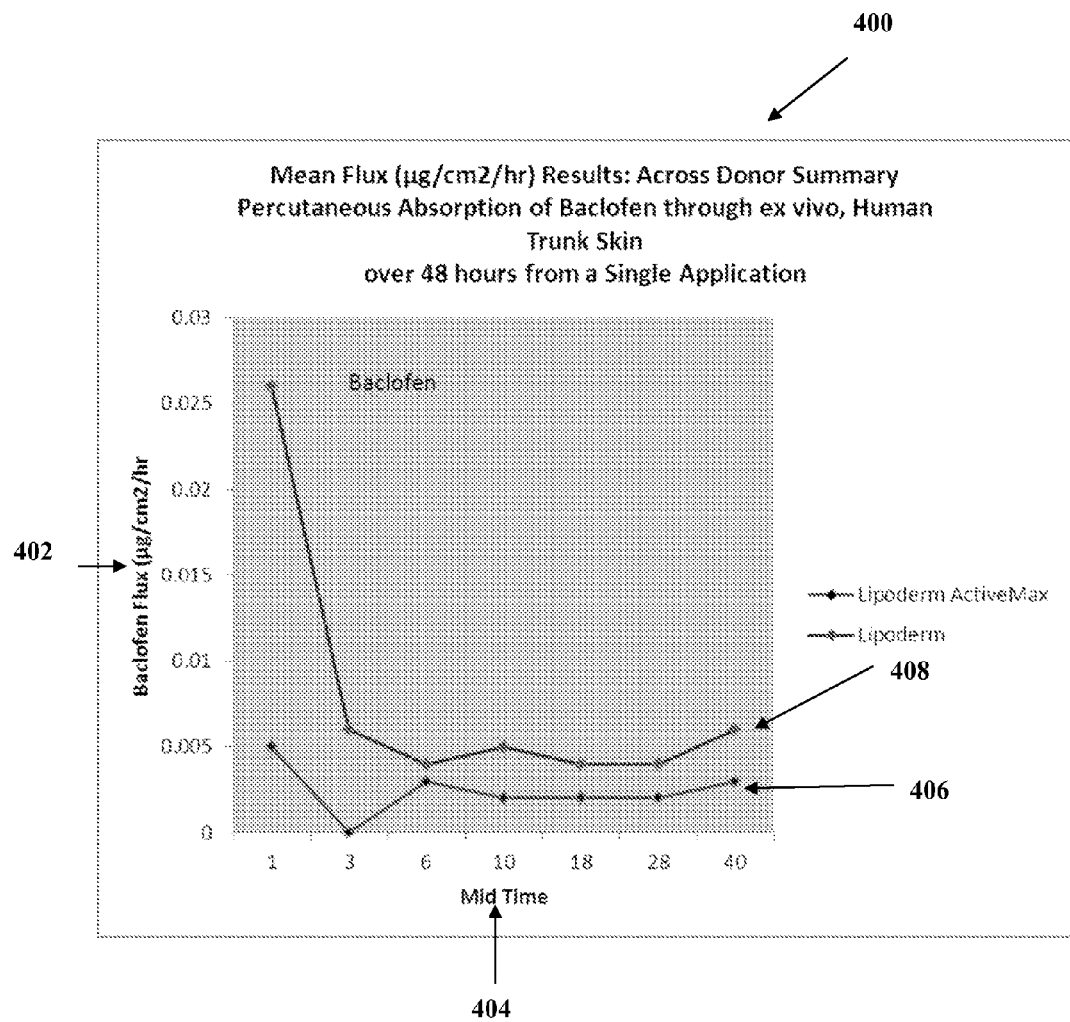
FIG. 4 depicts baclofen flux versus time exhibited during the exemplary evaluation.

FIG. 4 depicts baclofen flux versus time exhibited during the exemplary evaluation. In particular, FIG. 4 depicts a summary 400 of the mean flux ($\mu g/cm^2/hr$) 402 results of percutaneous absorption of baclofen through ex vivo, human trunk skin over 48 hours 404 from a single application. Depicted is the mean flux of baclofen through the skin using the base composition, Lipoderm® ActiveMax™ 406, and Lipoderm® 408.

Figure 5:
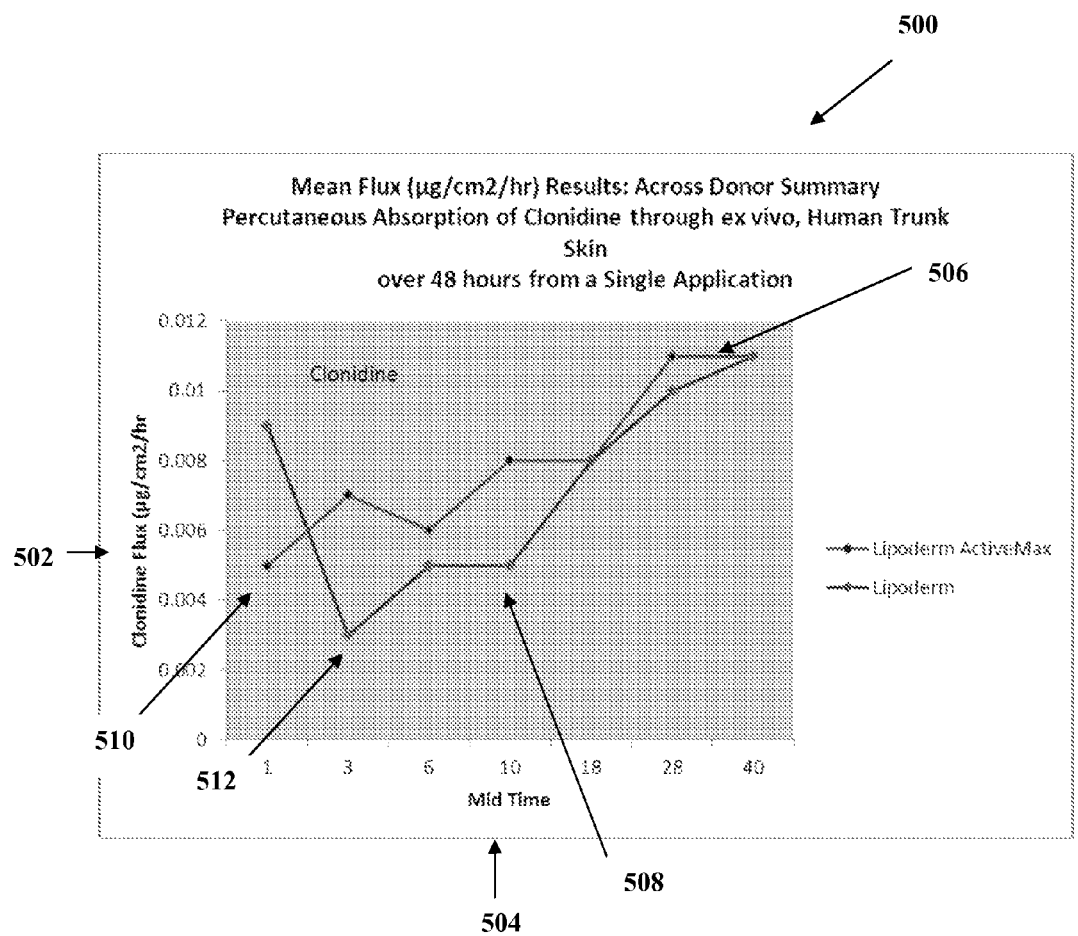
FIG. 5 depicts clonidine flux versus time exhibited during the exemplary evaluation.

FIG. 5 depicts clonidine flux versus time exhibited during the exemplary evaluation. In particular, FIG. 5 depicts a summary 500 of the mean flux ($\mu g/cm^2/hr$) 502 results of percutaneous absorption of clonidine through ex vivo, human trunk skin over 48 hours 504 from a single application. Depicted is the mean flux of clonidine through the skin using the base composition, Lipoderm® ActiveMax™ 506, and Lipoderm® 508.

The clonidine mean flux graph using the base composition, Lipoderm® ActiveMax™ 506, yielded a clonidine flux of approximately 0.005 $\mu g/cm^2/hr$ at about 1 hour after application, approximately 0.007 $\mu g/cm^2/hr$ at about 3 hours after application, approximately 0.006 $\mu g/cm^2/hr$ at about 6 hours after application, approximately 0.008 $\mu g/cm^2/hr$ at about 10 hours after application, approximately 0.008 $\mu g/cm^2/hr$ at about 18 hours after application, approximately 0.011 $\mu g/cm^2/hr$ at about 28 hours after application, and approximately 0.011 $\mu g/cm^2/hr$ at about 40 hours after application.

As shown in FIG. 5, the mean flux of clonidine through the skin using the base composition, Lipoderm® ActiveMax™ 506, was proven to exceed the mean flux of clonidine through the skin using Lipoderm® 508 from about two hours after application to about 40 hours after application. Also, the minimum mean flux of clonidine observed using the base composition 510 (at approximately 1 hour after application) also exceeded the minimum mean flux of clonidine through the skin observed using Lipoderm® 512 (at approximately 3 hours after application).

Figure 6:
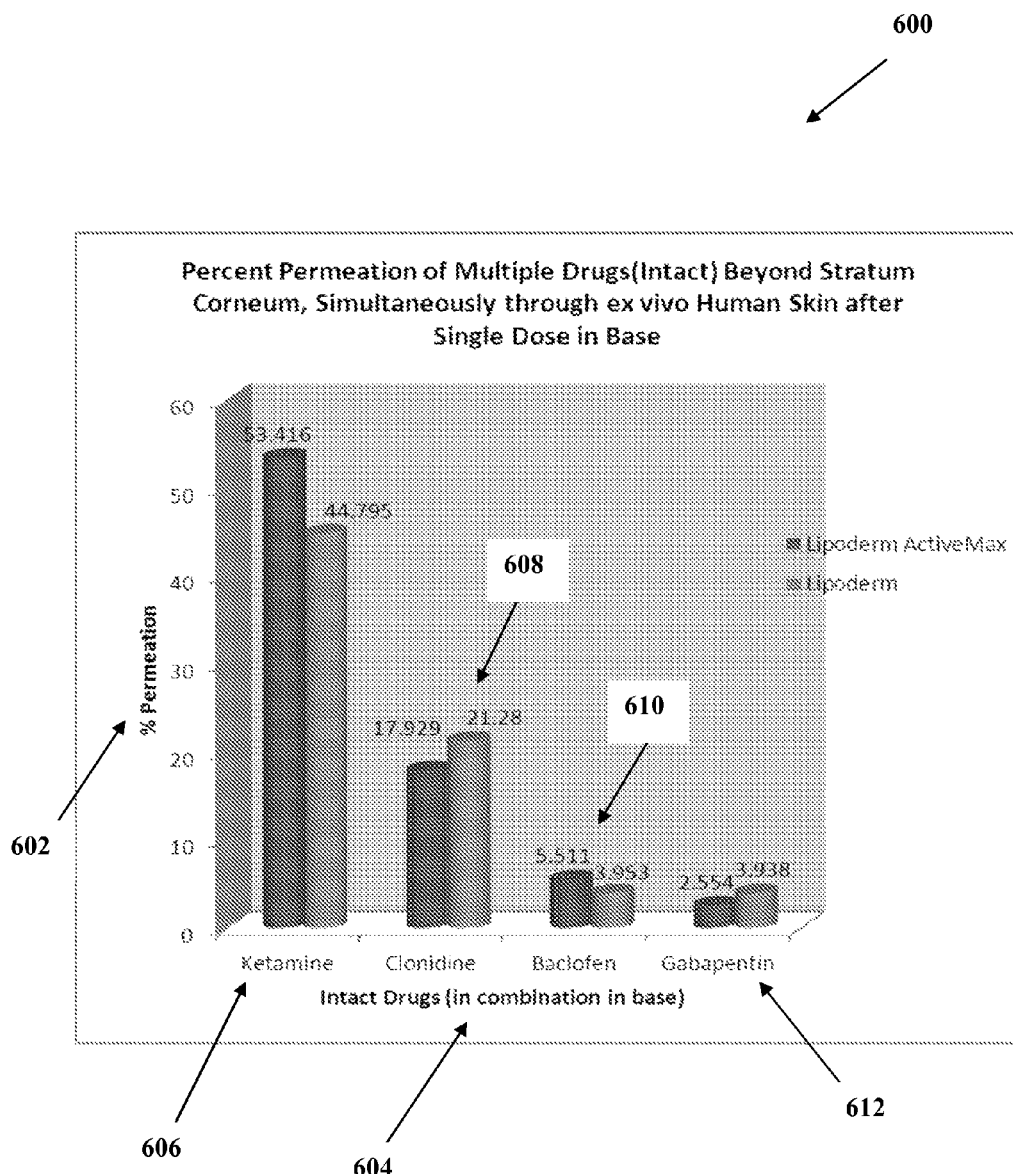
FIG. 6 depicts the total percentage permeation of the applied dose beyond the stratum corneum after a single dose of an exemplary transdermal cream is topically applied.

FIG. 6 depicts the total percentage permeation of multiple drugs (intact) beyond the stratum corneum simultaneously after a single dose of the exemplary transdermal cream embodiments is applied topically 600. In particular, FIG. 6 depicts comparisons of percent permeation 602 for four intact drugs topically applied in combination 604 via the base composition and Lipoderm®—comparisons for ketamine 606, clonidine 608, baclofen 610, and gabapentin 612.

As shown, the percent permeation for ketamine using the base composition, Lipoderm® ActiveMax™, was approximately 53.4%, which was substantially better than the approximately 44.8% percent permeation for ketamine achieved using Lipoderm® as a base. Also, the approximately 5.5% permeation of baclofen using the base composition, Lipoderm® ActiveMax™, was better than the approximately 3.95% permeation for baclofen achieved using Lipoderm® as a base. The base composition also yielded approximately 17.9% permeation for clonidine and approximately 2.6% permeation for gabapentin.

Exemplary formulations that were tested during the exemplary evaluation are listed below in Tables III and IV. "PCCA" identified below is the Professional Compounding Centers of America.

TABLE III

| Exemplary Lipoderm® Formula | |
| --- | --- |
| Ketamine HCL USP CIII | 5 gm |
| Gabapentin USP | 10 gm |
| Clonidine HCL USP | 0.2 gm |
| Baclofen USP | 2 gm |
| Propylene Glycol USP | 10 gm |
| Base, PCCA Lipoderm® q.s. | 100 gm |

TABLE IV

| Exemplary Lipoderm® ActiveMax™ Formula | |
| --- | --- |
| Ketamine HCL USP CIII | 5 gm |
| Gabapentin USP | 10 gm |
| Clonidine HCL USP | 0.2 gm |
| Baclofen USP | 2 gm |
| Propylene Glycol USP | 10 gm |
| Base, PCCA Lipoderm® ActiveMax™ q.s. | 100 gm |

IV. Other Exemplary Transdermal Cream Compositions

The base composition disclosed herein may be used with various total transdermal cream compositions. An exemplary transdermal cream composition may include approximately 30% or more ketamine HCL in the base composition. The transdermal cream composition may remain stable for six months or longer, and include active ingredient concentrations exceeding approximately 30%, and preferably approximately 40% or more, of the total formulation weight in some embodiments. The transdermal cream compositions may include vitamin E acetate, sodium metabisulfite, butylated hydroxytoluene, and Dow Corning® 200 Fluid. Exemplary ingredients to make 100 gm of transdermal cream are listed in Table V below.

TABLE V

| 30% Ketamine HCL Formulation | |
| --- | --- |
| To make 100 Gm: | |
| Ketamine HCL USP CIII | 30 Gm |
| Vitamin E Acetate (DL) USP Liquid (1 IU/MG) | 1 Gm |
| Sodium Metabisulfite NF Granular | 0.5 Gm |
| Butylated Hydroxytoluene NF (BHT) | 0.05 Gm |
| Dow Corning® 200 Fluid, 350 CST | 2 Gm |
| Lipoderm® ActiveMax™ q.s. | 100 Gm |

The amount of ketamine HCL in the exemplary transdermal cream listed above in Table V may be increased or decreased. For instance, the amount of ketamine HCL may be increased to approximately 40% or more of the transdermal cream by weight. Other active ingredients may also be added, such as gabapentin, baclofen, cyclobenzaprine, clonidine, flurbiprofen, amitriptyline, tramadol, lidocaine, prilocalne, and other medications as noted herein. Each active ingredient may comprise between approximately 0.01% and approximately 40% or more of the transdermal cream by weight. The total amount of active ingredients may comprise approximately 40% or more of the transdermal cream by weight.

Another exemplary transdermal cream composition may include approximately 79% of the base composition, along with approximately 10% flurbiprofen, approximately 1% amitriptyline, approximately 6% gabapentin, approximately 2% lidocaine, and/or approximately 2% prilocalne. Exemplary ingredients are listed in Table VI below.

TABLE VI

Flurbiprofen/Amitriptyline/Gabapentin/Lidocaine/Prilocaine Formulation

| Ingredients | Qty |
| --- | --- |
| Flurbiprofen | 100 mg |
| Amitriptyline | 10 mg |
| Gabapentin | 60 mg |
| Lidocaine | 20 mg |
| Prilocaine | 20 mg |
| Lipoderm ® ActiveMax ™ | 790 mg |

The amount of flurbiprofen, amitriptyline, gabapentin, lidocaine, and/or prilocalne in the exemplary transdermal cream listed above in Table VI may be increased or decreased. Other active ingredients may also be added, such as baclofen, cyclobenzaprine, clonidine, ketamine, tramadol, and/or other medications as noted herein. Each active ingredient may comprise between approximately 0.01% and approximately 40% or more of the transdermal cream by weight. The total amount of active ingredients may comprise approximately 40% or more of the transdermal cream by weight.

An exemplary transdermal cream composition may include approximately 79% of the base composition, along with approximately 10% flurbiprofen, approximately 1% cyclobenzaprine, approximately 6% gabapentin, approximately 2% lidocaine, and/or approximately 2% prilocalne. Exemplary ingredients are listed in Table VII below.

TABLE VII

Flurbiprofen/Cyclobenzaprine/Gabapentin/Lidocaine/Prilocaine Formulation

| Ingredients | Qty |
| --- | --- |
| Flurbiprofen | 100 mg |
| Cyclobenzaprine | 10 mg |
| Gabapentin | 60 mg |
| Lidocaine | 20 mg |
| Prilocaine | 20 mg |
| Lipoderm ® ActiveMax ™ | 790 mg |

The amount of flurbiprofen, cyclobenzaprine, gabapentin, lidocaine, and/or prilocalne in the exemplary transdermal cream listed above in Table VII may be increased or decreased. Other active ingredients may also be added, such as amitriptyline, baclofen, cyclobenzaprine, clonidine, ketamine, tramadol, and/or other medications as noted herein. Each active ingredient may comprise between approximately 0.01% and approximately 40% or more of the transdermal cream by weight. The total amount of active ingredients may comprise approximately 40% or more of the transdermal cream by weight.

Another exemplary transdermal cream composition may include approximately 86% of the base composition, along with approximately 10% gabapentin, approximately 2% lidocaine, and/or approximately 2% prilocalne. Exemplary ingredients are listed in Table VIII below.

TABLE VIII

Gabapentin/Lidocaine/Prilocaine Formulation

| Ingredients | Qty |
| --- | --- |
| Gabapentin | 100 mg |
| Lidocaine | 20 mg |
| Prilocaine | 20 mg |
| Lipoderm ® ActiveMax ™ | 860 mg |

The amount of gabapentin, lidocaine, and/or prilocalne in the exemplary transdermal cream listed above in Table VIII may be increased or decreased. Other active ingredients may also be added, such as flurbiprofen, amitriptyline, baclofen, cyclobenzaprine, clonidine, ketamine, tramadol, and/or other medications as noted herein. Each active ingredient may comprise between approximately 0.01% and approximately 40% or more of the transdermal cream by weight. The total amount of active ingredients may comprise approximately 40% or more of the transdermal cream by weight.

An exemplary transdermal cream composition may include approximately 70% of the base composition, along with approximately 30% ketamine. Ketamine may be provided as a 30% stand-alone compounded therapy to allow combination with a wide range of other therapies. Exemplary ingredients are listed in Table IX below.

TABLE IX

30% Ketamine Formulation

| Ingredients | Qty |
| --- | --- |
| Ketamine | 300 mg |
| Lipoderm ® ActiveMax ™ | 700 Mg |

The amount of ketamine in the exemplary transdermal cream listed above in Table V may be increased or decreased. For instance, the amount of ketamine may be increased to approximately 40% or more of the transdermal cream by weight. Other active ingredients may also be added, such as gabapentin, baclofen, cyclobenzaprine, clonidine, flurbiprofen, amitriptyline, tramadol, lidocaine, prilocalne, and/or other medications as noted herein. Each active ingredient may comprise between approximately 0.01% and approximately 40% or more of the transdermal cream by weight. The total amount of active ingredients may comprise approximately 40% or more of the transdermal cream by weight.

An exemplary compounded medication may include (1) an anti-inflammatory (non-steroidal), such as flurbiprofen, ibuprofen, meloxicam, and/or piroxicam; (2) a muscle relaxant, such as cyclobenzaprine; (3) a nerve pain depressant, such as gabapentin and/or topiramate; (4) a tricyclic anti-depressant, such as amitriptyline; (5) a local anesthetic, such as lidocaine and/or prilocalne; (6) an opioid or opiate agonist, such as tramadol; and/or (7) other anesthetics and/or pain suppressants, such as ketamine. Each active ingredient may comprise between approximately 0.01% and approximately 40% or more of the transdermal cream by weight. The total amount of compounded medication may comprise approximately 40% or more of a transdermal cream or gel by weight.

In general, the compounded medications may be used to treat generalized pain and/or muscle spasms. The combination therapies may assist patients by providing many different lines of medication in each application often without causing as many side effects as oral therapies. Each compounded transdermal cream may be applied in a small amount, such as the size of a quarter, to the site where the pain, inflammation, and/or swelling are localized.

V. Additionally Exemplary Compounded Formulas

The compounded formulas may be mixed to provide for formula quantities of 24,000 gm. For instance, an exemplary compound formula may include approximately 10% flurbiprofen, approximately 1% amitriptyline, approximately 6% gabapentin, approximately 2% lidocaine, and approximately 2% prilocalne in a transdermal gel. Exemplary ingredients are listed in Table X below.

TABLE X

Flurbiprofen/Amitriptyline/Gabapentin/Lidocaine/Prilocaine Formulation

| CHEMICAL | QUANTITY USED |
|---|---|
| FLURBIPROFEN USP | 2400.0 GM |
| AMITRIPTYLINE HYDROCHLORIDE | 240.0 GM |
| GABAPENTIN USP | 1440.0 GM |
| LIDOCAINE HYDROCHLORIDE USP MONOHYDRATE | 590.4 GM |
| PRILOCAINE HYDROCHLORIDE USP | 559.2 GM |
| VITAMIN E ACETATE USP LIQUID (1 IU/MG) | 240.0 GM |
| SODIUM METABISULFITE NF GRANULAR | 12.0 GM |
| BUTYLATED HYDROXYTOLUENE (BHT) | 12.0 GM |
| BASE, PCCA LIPODERM ACTIVEMAX | 18506.4 GM |

The amount of active ingredients in the exemplary transdermal cream listed above in Table X may be increased or decreased. Other active ingredients may also be added, such as baclofen, cyclobenzaprine, clonidine, ketamine, tramadol, and/or other medications as noted herein. Each active ingredient may comprise between approximately 0.01% and approximately 40% or more of the transdermal cream by weight. The total amount of active ingredients may comprise approximately 40% or more of the transdermal cream by weight.

With the formula listed above in Table X, lidocaine HCL monohydrate 1.23 gm=1 gm lidocaine base, and prilocalne HCL 1.165 gm=1 gm prilocalne base. The amount of each active ingredient needed should be calculated and weighed based on activity and adjust Lipoderm® ActiveMax™ accordingly. All ingredients should be combined in a 30 quart mixing bowl with at least 4000 grams of Lipoderm® ActiveMax™ on the bottom.

With a Globe SP30P set on the lowest speed of "1", a person preparing the mixture may set timer on the mixer to zero minutes and pulse slightly ¼ second per pulse until the powders are wet. The preparer should continue to stir on low for 15 minutes, and then allow the mixture to set for 45 minutes to thicken. The preparer should then stir for another 15 minutes. After which, mill in Exakt 120S-450 ointment mill with both rollers set to "1". The preparer should slowly adjust a rear roller to a setting of "3" to ensure that the product flows down the scraper plate appropriately. Then, the preparer should stir the milled product with the mixer set on "1" for 15 minutes and then package as desired in air-tight containers. The general procedure may be used with the formulations mentioned below as well.

Another exemplary compounded formula may include approximately 10% flurbiprofen, approximately 1% cyclobenzaprine, approximately 6% gabapentin, approximately 2% lidocaine, and approximately 2% prilocalne in a transdermal gel. The mixing or preparation instructions noted above may also be followed. Exemplary ingredients are listed in Table XI below.

TABLE XI

Flurbiprofen/Cyclobenzaprine/Gabapentin/Lidocaine/Prilocaine Formulation

| CHEMICAL | QUANTITY USED |
|---|---|
| FLURBIPROFEN USP | 2400.0 GM |
| CYCLOBENZAPRINE HYDROCHLORIDE | 240.0 GM |
| GABAPENTIN USP | 1440.0 GM |
| LIDOCAINE HYDROCHLORIDE USP MONOHYDRATE | 590.4 GM |
| PRILOCAINE HYDROCHLORIDE USP | 559.2 GM |
| VITAMIN E ACETATE USP LIQUID (1 IU/MG) | 240.0 GM |
| SODIUM METABISULFITE NF GRANULAR | 12.0 GM |
| BUTYLATED HYDROXYTOLUENE (BHT) | 12.0 GM |
| BASE, PCCA LIPODERM ACTIVE-MAX ® | 18506.4 GM |

The amount of active ingredients in the exemplary transdermal gel or cream listed above in Table XI may be increased or decreased. Other active ingredients may also be added, such as baclofen, amitriptyline, clonidine, ketamine, tramadol, and/or other medications as noted herein. Each active ingredient may comprise between approximately 0.01% and approximately 40% or more of the transdermal cream by weight. The total amount of active ingredients may comprise approximately 40% or more of the transdermal cream by weight.

Another exemplary compounded formula may include gabapentin, prilocalne, and/or other ingredients in a transdermal gel. The instructions noted previously may be followed to prepare the formula composition. Exemplary ingredients are listed in Table XII below.

TABLE XII

Gabapentin/Lidocaine/Prilocaine Formulation

| CHEMICAL | QUANTITY USED |
|---|---|
| GABAPENTIN USP | 2400.0 GM |
| LIDOCAINE HYDROCHLORIDE USP MONOHYDRATE | 590.4 GM |
| PRILOCAINE HYDROCHLORIDE USP | 559.2 GM |
| VITAMIN E ACETATE USP LIQUID (1 IU/MG) | 240.0 GM |
| SODIUM METABISULFITE NF GRANULAR | 12.0 GM |
| BUTYLATED HYDROXYTOLUENE (BHT) | 12.0 GM |
| BASE, PCCA LIPODERM ACTIVE-MAX | 20186.4 GM |

The amount of active ingredients in the exemplary transdermal cream listed above in Table XII may be increased or decreased. Other active ingredients may also be added, such as flurbiprofen, cyclobenzaprine, baclofen, amitriptyline, clonidine, ketamine, tramadol, and/or other medications as noted herein. Each active ingredient may comprise between approximately 0.01% and approximately 40% or more of the transdermal cream by weight. The total amount of active ingredients may comprise approximately 40% or more of the transdermal cream by weight.

Another exemplary compounded formula may include approximately 30% ketamine in a transdermal cream or gel. The instructions noted previously may be followed to prepare the formula composition. Exemplary ingredients are listed in Table XIII below.

TABLE XIII

Ketamine HCL Formulation

| CHEMICAL | QUANTITY USED |
|---|---|
| KETAMINE HCL USP | 7200.0 GM |
| VITAMIN E ACETATE USP LIQUID (1 IU/MG) | 240.0 GM |
| SODIUM METABISULFITE NF GRANULAR | 12.0 GM |
| BUTYLATED HYDROXYTOLUENE (BHT) | 12.0 GM |
| BASE, PCCA LIPODERM ACTIVE-MAX ® | 16536 GM |

The amount of ketamine in the exemplary transdermal cream listed above in Table XIII may be increased or decreased. Other active ingredients may also be added, such as flurbiprofen, cyclobenzaprine, gabapentin, lidocaine, prilocalne, baclofen, amitriptyline, clonidine, ketamine, tramadol, and/or other medications as noted herein. Each active ingredient may comprise between approximately 0.01% and approximately 40% or more of the transdermal cream by weight. The total amount of active ingredients may comprise approximately 40% or more of the transdermal cream by weight.

As shown in Table VII above, the compounded transdermal pain management program for the topical administration of multiple medications simultaneously may comprise: providing a transdermal cream; and providing several medications within the transdermal cream for topical administration to a patient. The several medications may include: (1) at least one local anesthetic in an amount between approximately 1.0% and approximately 7.0% of the transdermal cream by weight; (2) at least one nerve depressant in an amount between approximately 5.0% and approximately 15.0% of the transdermal cream by weight; (3) at least one NSAID (Non-Steroidal Anti-Inflammatory Drug) in an amount between approximately 5.0% and approximately 25.0% of the transdermal cream by weight; and (4) at least one muscle relaxant in an amount between approximately 0.5% and approximately 4.0% of the transdermal cream by weight such that multiple ailments are addressed simultaneously. The at least one local anesthetic may comprise both lidocaine and prilocalne, and the at least one nerve depressant may comprise gabapentin. The at least one muscle relaxant may comprise cyclobenzaprine, and the at least one NSAID may comprise flurbiprofen and/or nabumetone. In one embodiment, the transdermal cream may comprise, by weight of the transdermal cream, approximately 2.0% lidocaine, approximately 2.0% prilocalne, approximately 6.0% gabapentin, approximately 1.0% cyclobenzaprine, and approximately 10.0% flurbiprofen and/or approximately 20.0% nabumetone. The several medications may also include an opioid or opiate agonist in an amount between approximately 0.1% and approximately 10.0%; a tricyclic antidepressant in an amount between approximately 0.1% and approximately 4.0%; and/or a NMDA receptor antagonist in an amount between approximately 0.1% and approximately 40%.

As shown in Table VI above, a compounded transdermal pain management program for the topical administration of multiple medications simultaneously may comprise: providing a transdermal cream; and providing several medications within the transdermal cream for topical administration to a patient. The several medications may include: (1) at least one local anesthetic in an amount between approximately 1.0% and approximately 7.0% of the transdermal cream by weight; (2) at least one nerve depressant in an amount between approximately 5.0% and approximately 15.0% of the transdermal cream by weight; (3) at least one NSAID (Non-Steroidal Anti-Inflammatory Drug) in an amount between approximately 5.0% and approximately 25.0% of the transdermal cream by weight; and (4) at least one tricyclic antidepressant in an amount between approximately 0.5% and approximately 4.0% of the transdermal cream by weight such that multiple ailments are addressed simultaneously. The at least one local anesthetic may comprise both lidocaine and prilocalne, and the at least one nerve depressant may comprise gabapentin. The at least one tricyclic antidepressant may be amitriptyline, and the at least one NSAID may be flurbiprofen and/or nabumetone. In one embodiment, the transdermal cream may comprise, by weight of the transdermal cream, approximately 2.0% lidocaine, approximately 2.0% prilocalne, approximately 6.0% gabapentin, approximately 1.0% amitriptyline, and approximately 10.0% flurbiprofen and/or 20.0% nabumetone. The several medications may also include an opioid or opiate agonist in an amount between approximately 0.1% and approximately 10.0%; a muscle relaxant in an amount between approximately 0.1% and approximately 4.0%; and/or a NMDA receptor antagonist in an amount between approximately 0.1% and approximately 40%.

The present invention may be embodied in other forms without departing from the spirit or essential attributes thereof and, accordingly, reference should be had to the following claims rather than the foregoing specification as indicating the scope of the invention. Further, the illustrations are intended to provide a general understanding, and they are not intended to serve as a complete description of all the elements and features described herein. Other arrangements may be utilized and derived therefrom, such that logical substitutions and changes may be made without departing from the scope of this disclosure. Accordingly, the specification and drawings are to be regarded in an illustrative rather than a restrictive sense.

Thus, this disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A compounded transdermal pain management cream for topical administration of multiple medications simultaneously, the compounded transdermal pain management cream comprising:
    several medications within a base composition for topical administration to a patient, the several medications including
    at least one nerve depressant; at least one NSAID (Non-Steroidal Anti-Inflammatory Drug);
    at least one muscle relaxant;
    at least one opioid or opiate agonist;
    at least one local anesthetic, wherein the at least one local anesthetic is in an amount between approximately 1.0% and approximately 5% of the transdermal cream by weight; and at least one NMDA (N-Methyl-D-aspartate) receptor antagonist comprising ketamine in an amount of 30% to 40% of the transdermal cream by weight, and
at least one tricyclic antidepressant,
wherein the several medications comprise approximately 40% or more of the transdermal cream by weight.

* * * * *